United States Patent [19]

Burns

[11] Patent Number: 5,085,636
[45] Date of Patent: Feb. 4, 1992

[54] BALLOON CATHETER WITH INFLATION-DEFLATION VALVE

[75] Inventor: Matthew M. Burns, Minneapolis, Minn.

[73] Assignee: SciMed Life Systems, Inc., Maple Grove, Minn.

[21] Appl. No.: 596,573

[22] Filed: Oct. 11, 1990

Related U.S. Application Data

[63] Continuation of Ser. No. 297,078, Jan. 13, 1989, abandoned.

[51] Int. Cl.⁵ .............................................. A61M 29/02
[52] U.S. Cl. ..................................... 604/99; 604/167; 606/194
[58] Field of Search ............... 604/52, 53, 95–103, 604/104, 167, 247, 256; 128/657, 658, 772; 606/192–197, 199

[56] References Cited

U.S. PATENT DOCUMENTS

| | | | |
|---|---|---|---|
| 3,402,717 | 9/1968 | Doherty | 604/99 X |
| 3,675,658 | 7/1972 | Taylor | 604/98 |
| 3,707,151 | 12/1972 | Jackson | 604/96 |
| 3,726,283 | 4/1973 | Dye et al. | 604/99 |
| 4,085,757 | 4/1978 | Pevsner . | |
| 4,102,342 | 7/1978 | Akiyama | 128/325 |
| 4,213,461 | 7/1980 | Pevsner . | |
| 4,240,411 | 12/1980 | Hosono | 128/4 |
| 4,276,874 | 7/1981 | Wolvek et al. | 128/1 D |
| 4,281,660 | 8/1981 | Fujiwara | 128/642 |
| 4,285,341 | 8/1981 | Pollack | 604/101 |
| 4,413,989 | 11/1983 | Schjeldahl | 604/96 |
| 4,509,523 | 4/1985 | Pevsner . | |
| 4,545,367 | 10/1985 | Tucci | 128/344 |
| 4,598,707 | 7/1986 | Agdanowski et al. . | |
| 4,606,347 | 8/1986 | Fogarty et al. . | |
| 4,616,653 | 10/1986 | Samson et al. | 128/344 |
| 4,638,805 | 1/1987 | Powell . | |
| 4,646,742 | 3/1987 | Packard et al. | 128/344 |
| 4,665,925 | 5/1987 | Millar | 128/663 |
| 4,684,363 | 8/1987 | Ari et al. . | |
| 4,715,378 | 12/1987 | Pope, Jr. et al. | 606/194 |
| 4,762,129 | 8/1988 | Bonzel | 128/344 |
| 4,793,350 | 12/1988 | Mar et al. | 128/344 |
| 4,813,934 | 9/1989 | Engelson et al. . | |
| 4,819,637 | 4/1989 | Dormandy | 128/325 |
| 4,848,344 | 7/1989 | Sos et al. | 128/344 |
| 4,906,241 | 3/1990 | Noddin et al. | 606/194 |
| 4,932,959 | 6/1990 | Horzewski et al. | 606/194 |

FOREIGN PATENT DOCUMENTS 0371486 6/1990 European Pat. Off. .

Primary Examiner—John D. Yasko
Assistant Examiner—Adam J. Cermak
Attorney, Agent, or Firm—Kinney & Lange

[57] ABSTRACT

A balloon catheter for use with a guide wire in angioplasty includes a main shaft which is a flexible tube which has an inflatable balloon at its distal end. The inflatable balloon is attached at its proximal and distal ends to and surrounds a guide wire director. The guide wire extends through the catheter by extending through the shaft, through the guide wire director, and out the distal end of the balloon. Located within the interior of the balloon is an inflation valve and a deflation valve used to provide a fluid tight seal around the guide wire during balloon inflation and deflation.

27 Claims, 3 Drawing Sheets

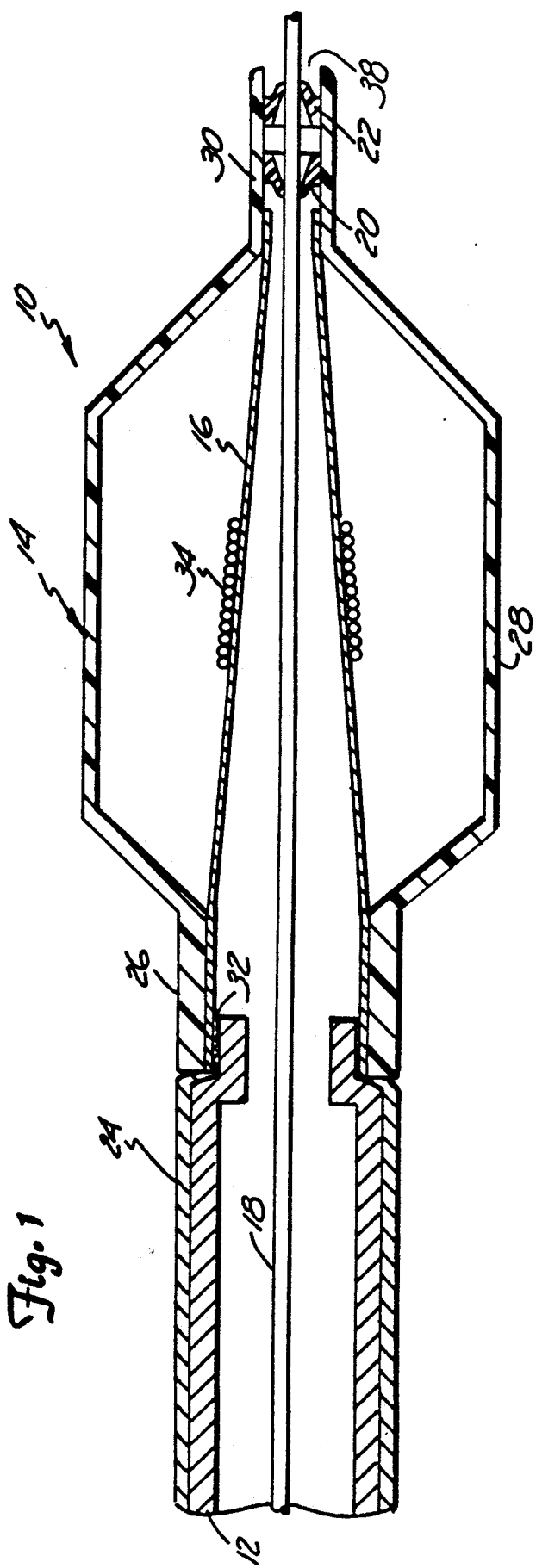

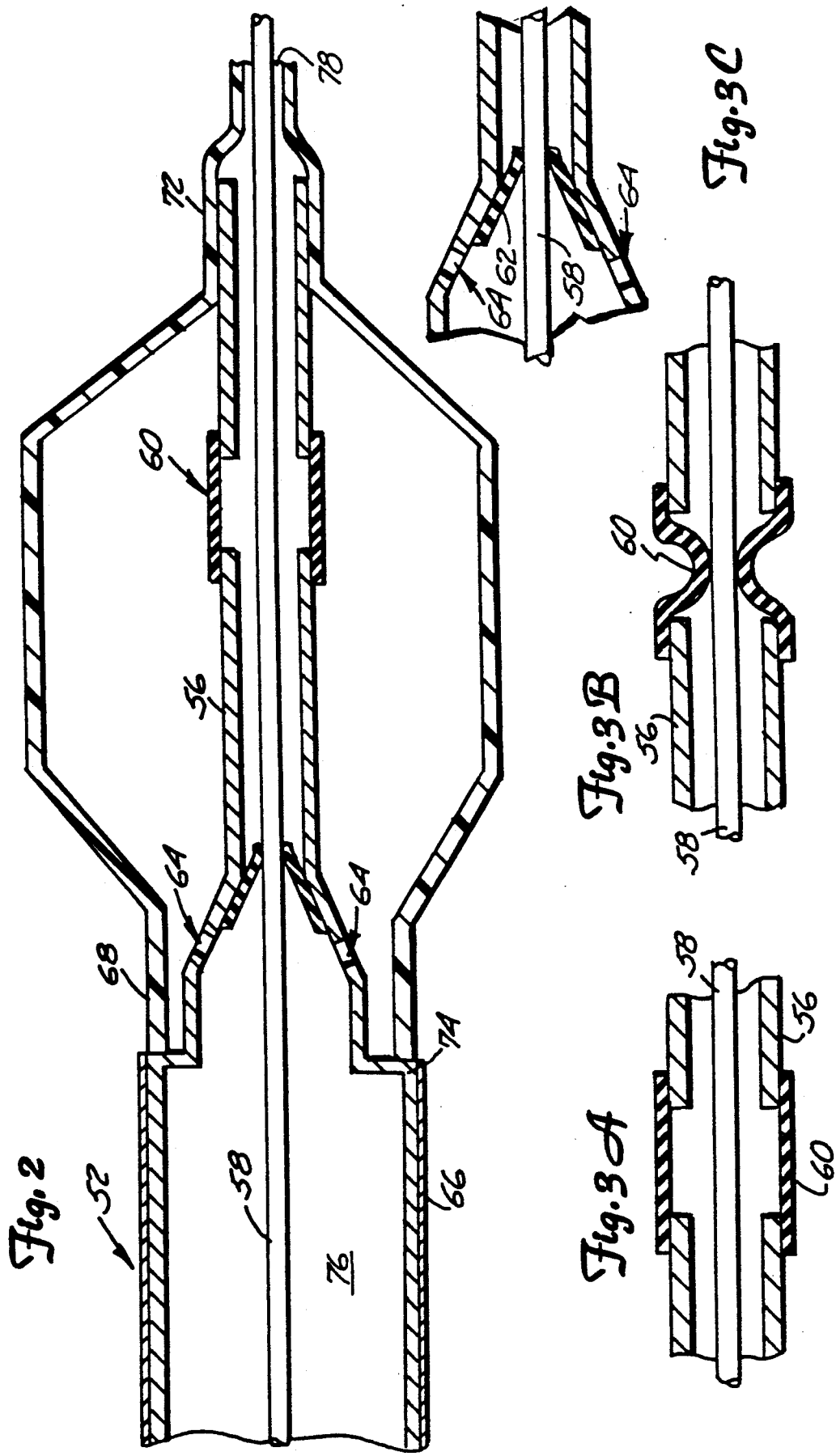

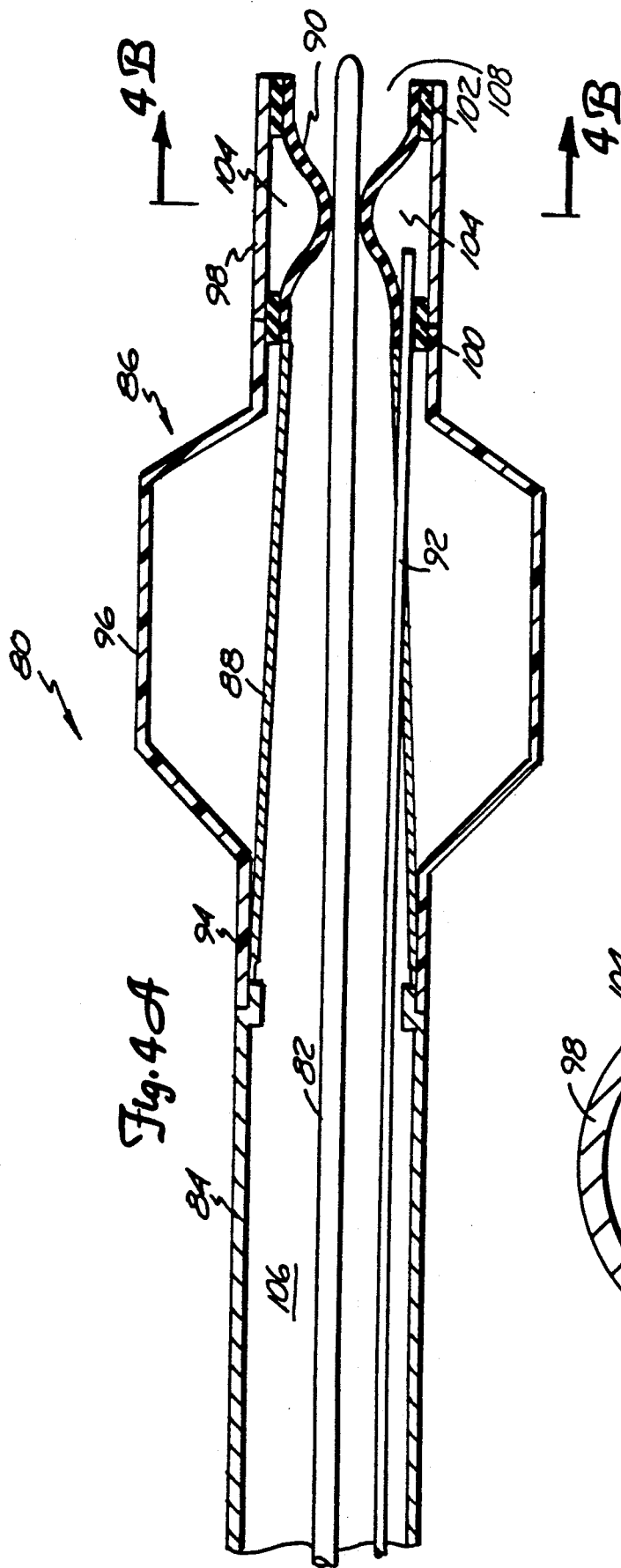
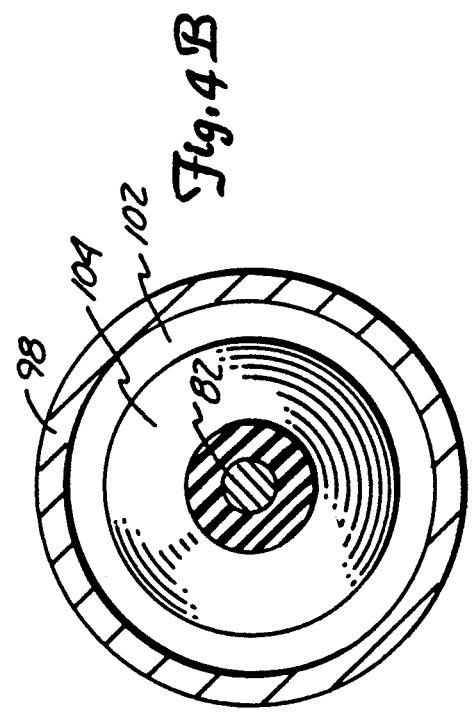

BALLOON CATHETER WITH INFLATION-DEFLATION VALVE

This is a continuation of application Ser. No. 297,078, filed Jan 13, 1989, now abandoned.

BACKGROUND OF THE INVENTION

1. Field of the Invention.

The present invention relates to the field of angioplasty. In particular, the present invention relates to a dilatation balloon catheter.

2. Prior Art.

Angioplasty has gained wide acceptance in recent years as an efficient and effective method for treating types of vascular diseases. In particular, angioplasty is widely used for opening stenoses in the coronary arteries, although it is also used for treatment of stenoses in other parts of the vascular system.

The most widely used form of angioplasty makes use of a dilatation catheter which has an inflatable balloon at its distal end. Using fluoroscopy, the physician guides the catheter through the vascular system until the balloon is positioned across the stenosis. The balloon is then inflated by supplying fluid pressure through an inflation lumen to the balloon. The inflation of the balloon causes stretching of the artery and pressing of the lesion into the artery wall to reestablish acceptable blood flow through the artery.

In order to treat very tight stenoses with small openings, there has been a continuing effort to reduce the profile (and shaft diameter) of the catheter so that the catheter cannot only reach but also cross very tight stenoses. A successful dilatation catheter must also be sufficiently flexible to pass through tight curvatures through the very tortuous path of the vascular system. A further requirement of a successful dilatation catheter is its "pushability".

This involves the transmission of longitudinal force along the catheter from its proximal end to its distal end so that a physician can push the catheter through the vascular system and the stenosis.

Two types of dilatation catheters are "over-the-wire" catheters and "non-over-the-wire" catheters. An over-the-wire catheter is one in which a separate guide wire lumen is provided so that a guide wire can be used to establish the path to the stenosis. The dilatation catheter can then be fed over the guide wire until the balloon is positioned within the stenosis. One problem with the over-the-wire catheter is the requirement of a larger profile (and shaft) in order to allow for the separate guide wire lumen.

A non-over-the-wire catheter acts as its own guide wire, and thus there is no need for a separate guide wire lumen. One advantage of a non-over-the-wire catheter is its potential for reduced profile (and shaft) since a guide wire lumen is not required. However, one disadvantage is the inability to maintain the position of the guide wire within the vascular system when removing the catheter and replacing it with one of a smaller (or larger) balloon diameter. Thus, with the non-over-the-wire catheter, the path to the stenosis must be reestablished when replacing the catheter with one having a different balloon diameter.

SUMMARY OF THE INVENTION

The catheter of the present invention is an over-the-wire catheter which does not require separate inflation and guide wire lumens. The catheter includes a main shaft, an inflatable balloon enclosing a guide wire director, and a means for providing a fluid tight seal around the guide wire. The shaft is an elongate hollow thin wall tube having a proximal end and a distal end, and having a lumen extending therethrough from the proximal end to the distal end. A first end of the inflatable balloon is connected to the distal end of the shaft and a proximal end of the guide wire director. A second end of the inflatable balloon is connected to a distal end of the guide wire director. The interior of the balloon is in fluid communication with the lumen of the shaft. The means for providing a fluid tight seal around the guide wire is positioned in the distal portion of the catheter to allow for inflation and deflation of the balloon.

In one preferred embodiment of the present invention, the guide wire director comprises a permeable material acting as a port communicating an inflation medium between the lumen and the balloon interior. The means for providing a fluid tight seal in order to inflate and deflate the balloon comprises inflation and deflation valves positioned in or near the distal end of the balloon which close on the guide wire during inflation and deflation of the balloon so as not to permit fluid leakage into/out of the second end of the balloon while inflating/deflating.

In another preferred embodiment of the present invention, the guide wire director is integral with and of similar construction to the main shaft, but has a smaller diameter. The guide wire director contains perforations which act as ports communicating an inflation medium between the lumen and the balloon interior. The means for providing a fluid tight seal comprises inflation and deflation valves positioned within the interior of the balloon which collapse onto the guide wire during application of positive or negative fluid pressure.

In still another embodiment, an inflatable/deflatable valve located in the balloon acts as the means for providing a fluid tight seal. The valve is controlled by fluid pressure/vacuum supplied through a small diameter tube extending through the interior of the shaft and the guide wire director.

BRIEF DESCRIPTION OF THE DRAWINGS

FIG. 1 is a sectional view of a first preferred embodiment of the balloon catheter of the present invention.

FIG. 2 is a sectional view of a second preferred embodiment of the balloon catheter of the present invention.

FIG. 3A is a detail view of the inflation valve shown in FIG. 2 under zero fluid pressure.

FIG. 3B is a detail view of the inflation valve shown in FIG. 2 collapsed upon the guide wire under 1 atm pressure within the balloon. FIG. 3C is a detail view showing collapse of the deflation valve on wire during application of a vacuum to the interior of the shaft.

FIGS. 4A and 4B are sectional views of a third preferred embodiment of the balloon catheter of the present invention.

DETAILED DESCRIPTION OF THE PREFERRED EMBODIMENTS

A catheter 10 shown in FIG. 1 is a dilatation balloon catheter, for use with guide wire 18, which includes catheter shaft 12, balloon member 14, guide wire director 16, inflation valve 20 and deflation valve 22.

Shaft 12 is an elongated flexible tube, preferably of stainless steel or polyimide with a low friction coating 24 such as Paralene or Teflon. Depending on the characteristics desired, shaft 12 can be of an integral or multipart construction. In the embodiment shown in FIG. 1, shaft 12 has an inside diameter of about 0.027 inch, an outside diameter of about 0.031 inch, and a shaft coating 24 thickness of about 0.0008 inch. Shaft 12 is mounted at its proximal end to an inflation device (not shown) which provides fluid under pressure to the lumen of shaft 12 for balloon inflation.

Balloon member 14, which is preferably a polymer material such as polyolefin, has a proximal or waist segment 26, a distensible balloon segment 28, and a small diameter distal segment 30. Proximal segment 26 is bonded to the distal end of shaft 12 and to the proximal end of guide wire director 16. Bonding material 32 is provided to seal together shaft 12 and guide wire director 16 with proximal segment 26 of balloon member 14.

In the embodiment shown in FIG. 1, guide wire director 16 extends through the interior of balloon member 14 with its diameter decreasing uniformly therethrough. The proximal end of guide wire director 16 is bonded by bonding material 32 (such as by an epoxy) to the distal end of shaft 12, and the distal end of guide wire director 16 is bonded to the distal segment 30 of balloon member 14. Guide wire director 16 is comprised of a permeable plastic material such that it acts as a port communicating an inflation medium between shaft 12 and balloon member 14. A radiopaque spring 34 surrounds guide wire director 16 at the central location of distensible balloon segment 28. Radiopaque spring 34 acts as a marker before the inflation medium is injected into and inflates distensible balloon segment 28. Thus, the physician can determine when balloon member 14 is properly positioned across the stenosis.

In FIG. 1, distal segment 30 of balloon member 14 contains inflation valve 20 and deflation valve 22 bonded therein. Guide wire 18 extends through shaft 12 and through balloon member 14. The inflation/deflation valve system permits guide wire 18 to pass through distal segment 30 of balloon member 14, but closes upon guide wire 18 during inflation and deflation of distensible balloon segment 28. Upon inflation, the inflation medium will pass through permeable plastic guide wire director 16 to inflate distensible balloon segment 28. Inflation valve 20 will simultaneously close on guide wire 18 thus providing a fluid tight seal. Upon deflation, the inflation medium will evacuate distensible balloon segment 28 by passing back through permeable plastic guide wire director 16. Deflation valve 22 will simultaneously close on guide wire 18 again providing a fluid tight seal. The inflation/deflation valve system of the present invention prevents any inflation medium from entering the vascular system during inflation, and prevents any blood or other body fluid from entering balloon catheter 10 during deflation.

A significant advantage of the present invention is the possibility for a very low profile catheter. Shaft 12 of catheter 10 acts as an inflation lumen as well as a guide wire path. Thus, a separate guide wire lumen is not required. The removal of the inner guide wire lumen (such as in a coaxial over-the-wire catheter) allows for a significantly smaller shaft 12.

FIG. 2 shows dilatation catheter 50, which is another embodiment of the present invention. Catheter 50, which is used in conjunction with guide wire 58, includes catheter shaft 52, balloon member 54, guide wire director 56, and valves 60 and 62.

Shaft 52 is an elongated flexible thin wall tube, preferably made of stainless steel or polyimide, with a low friction coating 66 such as Paralene or Teflon. Again, shaft 52 can be of an integral or multipart construction. Shaft 52 is mounted at its proximal end to an inflation device (not shown) which provides fluid under pressure to the lumen of shaft 52 for balloon inflation/vacuum deflation.

Balloon member 54, which is preferably a polymer material, has a proximal or waist segment 68, a distensible balloon segment 70, and a small diameter distal segment 72. Proximal segment 68 is bonded to the distal end of shaft 52 and to the proximal end of guide wire director 56.

In the embodiment shown in FIG. 2, guide wire director 56 extends through the interior of balloon member 54 with its diameter increasing near proximal segment 68. Guide wire director 56 is integral with and the same entity as shaft 52, and is thus a non-porous material. The distal end of guide wire director 56 is bonded to distal segment 72 of balloon member 54. Perforations 64 in guide wire director 56 act as a port communicating an inflation medium between shaft 52 and the interior of balloon member 54.

In FIG. 2, inflation valve 60 and deflation valve 62 are shown. Inflation valve 60 and deflation valve 62 are preferably made of flexible polymeric material. Guide wire 58 extends through shaft 52, through balloon member 54, and out of and beyond distal segment 72 of balloon member 54 and the distal end of guide wire director 56. Upon inflation, an inflation medium passes through perforations 64 to inflate distensible segment 70 of balloon member 54. Inflation valve 60 simultaneously closes on guide wire 58, thus providing a fluid tight seal between inflation valve 60 and guide wire 58. FIG. 3A shows inflation valve 60 in FIG. 2 under zero inflation medium pressure. FIG. 3B shows inflation valve 60 collapsed upon guide wire 58 during inflation under 1 atm inflation medium pressure. Upon deflation, the inflation medium evacuates distensible balloon segment 70 by passing back through perforations 64 of non-porous guide wire director 56. As shown in FIG. 3C, deflation valve 62 simultaneously closes on guide wire 58, providing a fluid tight seal between valve 62 and guide wire 58.

FIGS. 4a and 4b show dilatation catheter 80, which is still another embodiment of the present invention. Catheter 80 is used in conjunction with guide wire 82. Catheter 80 includes shaft 84, balloon member 86, guide wire director 88, bladder valve 90, and bladder inflation/deflation tube 92. Catheter 80 is an over-the-wire type of dilatation balloon catheter which is moveable with respect to guide wire 82.

Shaft 84 is an elongated, flexible tube which may be of a single or multipart construction. In one preferred embodiment, shaft 84 is a stainless steel or polyimide material, with a low friction coating.

Balloon member 86, which is preferably a polymer material, has a proximal or waist portion 94, a distensible balloon segment 96, and a distal segment 98. Proximal segment 94 of balloon member 86 is bonded or otherwise attached to the distal end of shaft 84.

Guide wire director 88 extends through the interior of balloon member 86. Guide wire director 88 is permeable, to allow fluid communication between the lumen of shaft 84 and the interior of distensible segment 96 of balloom member 86. The proximal end of guidewire director 88 is bonded or otherwise attached to the distal end of shaft 84, the proximal segment 94 of balloon member 86, or both.

At its distal end, guide wire director 88 is attached to bladder valve 90 within the interior of distal segment 98. The distal end of guide wire director 88, and the proximal end of bladder valve 90 are attached by a ring 100 of a bonding material (such as epoxy) to the interior of distal segment 98. A second ring 102 of bonding material attaches the distal end of bladder valve 90 to the interior of distal segment 98 of balloon member 86.

Tube 92 extends from the proximal end of catheter 80 through shaft 84 and the interior of balloon member 86 into cavity 104, which is an annular cavity defined by bladder valve 90, distall segment 98, and rings 100 and 102 of bonding material. Bladder valve 90 can be inflated so as to surround and form a fluid-type seal around guide wire 82 by applying fluid under pressure through tube 92 to cavity 104. Bladder 90 is inflated by a low viscosity fluid to act as a shut off valve during inflation and deflation of balloon segment 96. In this embodiment, the lumen of shaft 84 and the inner lumen of tube 92 are attached to separate manifolds (not shown) at the proximal end of catheter 80.

As mentioned, the shaft can be of multipart construction. For example, in a typical catheter shaft of approximately 54 inches, the first 42 inches from the proximal end of the shaft are "hypotube" (stainless steel hypodermic needle tube), while the last 12 inches are a flexible polymer tube (e.g., HDPE). In this case, the distal end of the hypotube and proximal end of the flexible polymer tube are bonded together, and the distal end of the flexible polymer tube and proximal end of the balloon member are bonded together (or the flexible polymer tube and balloon member may be integral). Indeed, in one embodiment, the shaft and balloon member are integrally formed from a suitable polymer material.

Although the present invention has been described with reference to preferred embodiments, workers skilled in the art will recognize that changes may be made in form and detail without departing from the spirit and scope of the invention.

What is claimed is:

1. An angioplasty balloon catheter assembly comprising:
    a guide wire;
    a shaft having a proximal end and a distal end, and having a lumen which extends longitudinally therethrough from the proximal end to the distal end and which is adapted to receive the guide wire therein;
    an inflatable balloon at the distal end of the shaft and having an interior in fluid communication with the lumen;
    director means connected to the distal end of the shaft and extending through the balloon to the distal end of the balloon for defining a path for the guide wire from the lumen, through the balloon and distally therefrom;
    first valve means positioned across the path which permits movement of the guide wire freely therethrough for providing a fluid tight seal across the path only when positive fluid pressure is applied through the lumen to the interior of the balloon; and
    second valve means positioned across the path which permits movement of the guide wire freely therethrough for providing a fluid tight seal across the path only when net negative fluid pressure is created in the lumen and balloon interior for deflation thereof.

2. The catheter assembly of claim 1 wherein the director means has a port fluidly communicating between the lumen and the interior of the balloon.

3. The catheter assembly of claim 1 wherein a first end of the balloon is bonded to the distal end of the shaft and to the proximal end of the director means.

4. The catheter assembly of claim 3 wherein a second end of the balloon is bonded to the distal end of the director means.

5. The catheter assembly of claim 1 wherein the balloon has a proximal waist segment, an intermediate balloon segment, and a distal segment.

6. The catheter assembly of claim 5 wherein the first valve means is positioned in the distal segment of the balloon.

7. The catheter assembly of claim 5 wherein the second valve means is positioned in the distal segment of the balloon.

8. The catheter assembly of claim 5 wherein the first valve means is located within the intermediate balloon segment of the balloon.

9. The catheter assembly of claim 8 wherein the first valve means comprises a ring-shaped inflation valve which collapses against and seals around the guide wire to provide a fluid tight seal upon xposure to positive fluid pressure in the balloon interior.

10. The catheter assembly of claim 5 wherein the second valve means is positioned in the intermediate balloon segment of the balloon.

11. The catheter assembly of claim 5 wherein the second valve means is positioned adjacent the proximal waist segment of the balloon.

12. The catheter assembly of claim 1 wherein the valve is bonded to a distal segment of the balloon.

13. The catheter assembly of claim 1 wherein the first and second valve means are spaced apart longitudinally.

14. The catheter assembly of claim 13 wherein the first valve means is disposed proximally of the second valve means.

15. An angioplasty balloon catheter assembly comprising:
    a guide wire;
    a shaft having a proximal end and a distal end, and having a lumen which extends longitudinally therethrough from the proximal end to the distal end and which is adapted to receive the guide wire therein;
    an inflatable balloon at the distal end of the shaft and having an interior in fluid communication with the lumen
    director means connected to the distal end of the shaft and extending through the balloon to the distal end of the balloon for defining a path for the guide wire from the lumen, through the balloon and out the distal end of the balloon; and
    a valve positioned across the path for the guide wire defined by the director means which permits movement of the guide wire freely therethrough and has an inflation state wherein a portion of the valve closes upon the guide wire to provide a fluid tight seal across the path for the guide wire when positive fluid pressure is applied through the lumen to the interior of the balloon and a deflation state wherein a portion of the valve closes upon the guide wire to provide a fluid tight seal across the path for the guide wire when net negative fluid pressure is created in the lumen and balloon interior, with that portion of the valve which provides a fluid tight seal when net negative fluid pressure is created being a deflation valve which collapses against and seals around the guide wire to provide a fluid tight seal upon exposure to net negative fluid pressure in the balloon.

16. The catheter assembly of claim 15 wherein that portion of the valve which provides a fluid tight seal when net positive pressure is created is disposed distally of that portion of the valve which provides a fluid tight seal when net negative pressure is created.

17. The catheter assembly of claim 15 wherein the director means has a port fluidly communicating between the lumen and the interior of the balloon, with the port being disposed proximally from that portion of the valve which provides a fluid tight seal when net negative pressure is created.

18. An angioplasty balloon catheter for use with a guide wire, the balloon catheter comprising:
 a shaft having a proximal end and a distal end, and having a lumen extending therethrough from the proximal end to the distal end;
 an inflatable balloon at the distal end of the shaft and having an interior in fluid communication with the lumen;
 director means connected to the distal end of the shaft and extending through the balloon to the distal end of the balloon for defining a path for the guide wire from the lumen, through the balloon and out the distal end of the balloon;
 an inflatable bladder positioned across the path for the guide wire to provide a fluid tight seal between the balloon and the guide wire when the bladder is inflated so that the balloon is inflatable only when the bladder is inflated to form said seal with the guide wire; and
 means for selectively inflating and deflating the bladder independently of balloon inflation and deflation.

19. The catheter of claim 18 wherein the inflatable bladder is an annular bladder.

20. The catheter of claim 18 wherein the inflatable bladder is positioned in a distal segment of the balloon.

21. The catheter of claim 18 wherein he means for selectively inflating and deflating the bladder is a bladder inflation tube which extends proximally from the bladder through the lumen of the shaft to its proximal end.

22. An angioplasty balloon catheter assembly comprising:
 a shaft having a proximal end and a distal end, and having a single lumen extending therethrough from the proximal end to the distal end;
 a director having a proximal end and a distal end, the director being connected to and extending distally from the distal end of the shaft, with the director defining a distal extension for the single lumen of the shaft and having liquid permeable walls;
 a guide wire movably extending through the lumen of the shaft and the director;
 an inflatable balloon having a proximal end and a distal end, the balloon being sealably connected at its proximal end to the distal end of the shaft and at its distal end to the distal end of the director, with the balloon surrounding the director and having its interior in liquid communication with the lumen through the liquid permeable walls of the director; and
 valve means adjacent the distal end of the balloon for providing an essentially fluid-tight seal around the guide wire during inflating and deflating of the balloon at any selected point along the guide wire relative to the balloon.

23. The catheter assembly of claim 22 wherein the director has a port communicating between the lumen and the interior of the balloon.

24. The catheter assembly of claim 22 wherein the balloon has a proximal waist segment, an intermediate balloon segment, and a distal segment.

25. The catheter assembly of claim 22 wherein the valve means for providing an essentially fluid tight seal around the guide wire comprises:
 an inflatable bladder positioned to provide a seal between the balloon and the guide wire when the bladder is inflated; and
 means for selectively inflating and deflating the bladder independently of balloon inflation and deflation.

26. The catheter of claim 25 wherein the inflatable bladder is an annular bladder.

27. The catheter of claim 25 wherein the means for selectively inflating and deflating the bladder is a bladder inflation tube which extends proximally from the bladder through the lumen of the shaft to its proximal end.

* * * * *

UNITED STATES PATENT AND TRADEMARK OFFICE
CERTIFICATE OF CORRECTION

PATENT NO. : 5,085,636
DATED : February 4, 1992
INVENTOR(S) : Matthew M. Burns

It is certified that error appears in the above-identified patent and that said Letters Patent is hereby corrected as shown below:

Col. 6, Line 27, delete "xposure", insert "exposure"

Col. 6, Line 52, after "lumen", insert a ";"

Col. 7, Line 48, delete "he", insert "the"

Signed and Sealed this

Ninth Day of November, 1993

Attest:

BRUCE LEHMAN

Attesting Officer    Commissioner of Patents and Trademarks